United States Patent [19]

Robertson

[11] Patent Number: 5,340,309

[45] Date of Patent: Aug. 23, 1994

[54] APPARATUS AND METHOD FOR RECORDING JAW MOTION

[76] Inventor: James G. Robertson, 601 Van Ness Ave., #424, San Francisco, Calif. 94102

[21] Appl. No.: 579,330

[22] Filed: Sep. 6, 1990

[51] Int. Cl.$^5$ .......................... A61C 19/04; A61C 5/00
[52] U.S. Cl. .................................... 433/69; 433/215
[58] Field of Search ........................ 433/68, 69, 215

[56] References Cited

U.S. PATENT DOCUMENTS

| | | | |
|---|---|---|---|
| 3,307,262 | 3/1967 | Chaiken | 32/19 |
| 4,405,940 | 9/1983 | Woolfson et al. | 358/93 |
| 4,447,207 | 5/1984 | Kataoka et al. | 433/69 |
| 4,495,952 | 1/1985 | Klett | 128/777 |
| 4,561,846 | 12/1985 | Polizzotto | 433/73 |
| 4,575,805 | 3/1986 | Moermann et al. | 364/474 |
| 4,634,377 | 1/1987 | Behrend | 433/73 |
| 4,811,093 | 3/1989 | Giacometti | 358/106 |
| 4,836,778 | 6/1989 | Baumrind et al. | 433/69 |
| 4,843,460 | 6/1989 | Le Guet et al. | 358/107 |
| 4,859,181 | 8/1989 | Neumeyer | 433/69 |
| 4,976,618 | 12/1990 | Anderson | 433/215 |

OTHER PUBLICATIONS

S. King and A. Mukerjee, "Inexact Visualization: Qualitative Object Representation for Recognizable Reconstruction," First Conference on Visualization in Biomedical Computing, (May 22-25, 1990).
R. E. Fredericksen, J. M. Coggins, T. J. Cullip, S. M. Pizer, "Interactive Object Definition in Medical Images Using Multiscale, Geometric Image Descriptions," First Conference on Visualization in Biomedical Computing (May 22-25, 1990).
Mitchelson, "Automated Three Dimensional Movement Analysis Using the CODA-3 System, Biomedizinische Technik," Band 33, Heft Jul.-Aug. 1988.
Y. Suzuki and K. Tsuchiya, "ADL motion analyses" by selspot, Biomechanics VII-A, International Series on Biomechanics, vol. 3A, University Park Press (1981).
V. Macellari, M. Rossi, and M. Bugarini, "Human Motion Monitoring Using the CoSTEL System with Reflective Markers," Biomechanics IX-B, Human Kinetics Publishers (1985).
H. J. Woltring, "New Possibilities for Human Motion Studies by Real-Time Light Spot Position Measurement," Laboratory of Psychology, University of Nijmegen, Erasmuslaan 16, NL-6804 Nijmegen (The Netherlands).
Mandibular Motion Analysis System Phase II SBIR Final Report, Jun. 1991.

*Primary Examiner*—Gene Mancene
*Assistant Examiner*—Cindy A. Cherichetti
*Attorney, Agent, or Firm*—Limbach & Limbach

[57] ABSTRACT

A method and apparatus for tracking, recording and analyzing a subject's jaw motion is provided. Crosshaired targets are non-intrusively fixed in relation to the subject's upper and lower jaws. Three video cameras are disposed about the subject's head, each camera lens being focused on the targets. Each video camera is equipped with a charge control device chip which includes an array of light sensitive pixels defining a two dimensional image coordinate system. The charge control device chip converts a light image indicative of a target's cross-hair position into a series of amplitude signals. A computer is used to receive, process and display said camera chip amplitude signals. The computer includes a pre-processor board for timing, synchronizing and transforming said camera chip amplitude signals into address record information representing the targets' relative positions as a function of time. The computer also has a mass storage unit for storing address record information, graphics software for creating a simulation of the subject's jaw movement in the subject coordinate system based on the address record information, and a display for visually presenting the simulation produced by the graphics software. The method and apparatus are useful for understanding orofacial pain, fabricating prosthesis, analyzing temporomandibular joint dysfunction pathology and orthodontic and occlusion problems.

7 Claims, 8 Drawing Sheets

FIG. 1A TARGET

APPARATUS AND METHOD FOR RECORDING JAW MOTION

FIELD OF THE INVENTION

The present invention relates generally to jaw motion tracking and recording instruments, and more particularly to the use of positional data collected by video cameras, translated and stored in a computer. The data is useful in the production of screen display simulations, dental pantographs or electronic articulator control for diagnostic and therapeutic purposes.

BACKGROUND OF THE INVENTION

The dental pantograph is currently the primary instrument for measuring jaw motion. The pantograph provides motion envelope tracings on paper. Some models interface electronically with a computer for positional data processing. The pantograph device does not accurately measure the six-dimensional space of movement present between upper and lower jaws.

The pantograph device is cumbersome because it must be clamped to the patient's head, and thereby restricts complete freedom of movement and precludes measurements of normal jaw chewing and talking motions. It requires significant set up time and is very technique-sensitive. Because of these shortcomings, the pantograph is seldom used in actual practice except for very specialized reconstructive work.

Previous investigators have attempted to overcome the pantograph's deficiencies. These efforts have contributed to an evolutionary improvement in the technology and a better understanding of the clinical requirements. The following discussion, however, is limited to devices for measuring jaw motion and does not include more generalized instruments.

One such device uses a magnet placed in the mouth with sensors around the head. This device records only the three dimensions of translation and not rotation. Consequently, it is of limited value.

Another device uses fiber optics and custom semiconductor light sensitive arrays to measure the relative motion between the upper and lower jaw. This device requires a cumbersome apparatus to be worn by the patient which actually prevents measurements during normal oral activity. It also requires very expensive, custom semiconductor components which render it commercially impractical.

Another device, a Kinesiograph, uses magnets and pickup coils to display the mandible motion on an oscilloscope. This device requires the patient to wear an apparatus which precludes normal oral activity during testing. It suffers from linearity problems and presents a fleeting analog display that is difficult to analyze with a computer.

Another device uses two arrays of ultrasound devices, one held in the lower jaw with a jaw plate and the other strapped to the head. The ultrasound transmitters are pulsed sequentially. The sound signals are received at three points that define a plane. By measuring the transit time for the ultrasound signals, it is possible to determine the relative position of the transmitters and receivers. This device also suffers from the problem that an uncomfortable device must be held in the mouth which prevents normal oral activity. In addition, the electronic specifications for reliable and accurate operation are very demanding making it too costly. A number of other devices using light emitting diodes and various sensor arrangements have been tried. These devices add the benefit of real time measurement and have incrementally advanced the art but fail to achieve all the objectives of a useful instrument. In particular, these devices fail to achieve unencumbered oral freedom of movement during measurement or to provide accurate 3-dimensional measurement.

Baumrind et al., U.S. Pat. No. 4,836,778, have advanced the LED array method to the point where they are able to measure the movement of the cranium and lower jaw independently with respect to a reference and also to measure rotation and translation on all axes (six degrees of freedom). This device, however, still requires the patient to wear a harness of illuminated LEDs. It also requires significant set up and adjustment and a calibration process. The distance between the patient and the sensors must be kept constant after calibration. The sensors are subject to calibration shifts and can vary during the time of the test. With this method, a large part of the measurement function is passed onto the computer where specialized software processes the data.

There are other, more general, body motion tracking devices both in use and under development. These other devices are expensive and too generalized to be practical for the specific application to the mandible discussed here.

The present instrument provides a means to record and analyze jaw motion. It incorporates innovative techniques to obtain a level of performance not presently available. This performance will open the doors to clinical techniques not presently practical. In addition it may bring greater awareness of oral motor pathologies and may aid in the evolution of new clinical practices to treat these pathologies.

Those skilled in the art will appreciate the numerous possible applications for this invention. It is a tool that can provide detailed information where previously only imprecise information was available. Awareness of the usefulness of this information will grow with experience.

Therefore, it is an object of the present invention to provide an apparatus and method for collecting and recording data representative of jaw movement, including rotational and translational motion along each of three axes of a three dimensional Cartesian coordinate system.

Another object of the invention is to provide a computer generated simulation of the subject's jaw movement on a screen display, which can be analyzed and manipulated through the use of software.

Another object of the invention is to provide an apparatus and method for electronically producing a dental pantograph.

Another object of the invention is to provide an apparatus and method for electronically adjusting an articulator for diagnostic and/or therapeutic purposes.

SUMMARY OF THE INVENTION

The above objects are accomplished by the present invention, which in a preferred embodiment includes two targets, each of which are adapted to be non-intrusively attached to the subject's teeth. One of the targets is attached to a frontal tooth in the subject's upper jaw, and the other target is similarly attached to a tooth in the lower jaw. The targets have cross-hairs of high optical contrast relative to its colored background.

Three video cameras are located about the subject's head along camera coordinates X, Y and Z, each camera being positioned so that its lens is focused on the targets' cross-hairs. Each camera has a charge control device chip (CCD) including an array of light sensitive pixels defining a two dimensional image coordinate system for converting a light image indicative of a target's cross-hair position into a series of amplitude signals.

A computer receives and processes the amplitude signals produced by the cameras. The computer includes a pre-processor board for timing, synchronizing and transforming the amplitude signals received from each camera into an address record representing the targets' relative positions as a function of time. The computer also has a mass storage unit for storing the address record, and graphics hardware and software for converting the address record into a screen display image of the subject's jaw movement in the subject coordinate system.

The screen display image may be printed to produce a dental pantograph. The data may also be used to drive motors to adjust an articulator. Each of the uses for the computer recorded data may be useful for understanding orofacial pain, fabricating prosthesis, analyzing temporomandibular joint dysfunction pathology and orthodontic and occlusion problems.

DETAILED DESCRIPTION OF THE INVENTION

A preferred embodiment of the invention includes at least three video cameras (x, y, and z axis), a pre-processing board, a computer, high resolution video display, other input/output devices, processing software and targets for the patient. The targets are fixed to the patient's upper and lower jaw. The video cameras transmit the position and motion of the affixed targets with six degrees of freedom to a data pre-processing board inside a desk-top computer.

The pre-processing board extracts the raw target, position information from the video image data and makes this data available to the computer for storage and processing. Advanced Artificial Intelligence (AI) techniques including Fuzzy logic are employed in the pre-processor and software to obtain a target position from the video image data with high accuracy and reliability.

The target position data can then be recalled from data storage, and displayed in a generalized three dimensional solid graphical format under the user's control. The graphics are displayed and, optionally, printed. The data can also be manipulated to drive motors to adjust an articulator.

The three dimensional graphical display reveals the boundary of jaw motion paths. It is possible to display the patient's teeth in relative motion in a three dimensional format. The operator can then manipulate the lower teeth relative to the upper teeth on the video display.

The graphical display of the teeth requires first using the frontal camera to focus on the patient's mouth at his upper and lower teeth, and then, second, tracing the image on the video display using a mouse. Some physical measurements must also be taken separately and then entered into the computer to correctly scale and orient the teeth image. Optionally, one of a number of "standard" teeth sets can be used for the display.

Motion data is collected during normal activities such as speech, chewing, maximum jaw extension and swallowing. The data includes velocities, envelope of motion, asymmetries of movement, and possibly information on condyle movement within their envelopes. This data is useful in understanding chronic orofacial pain, in prosthesis fabrication, An analysis of temporomandibular pathology, in orthodontics and in occlusion analysis.

Figure 1:
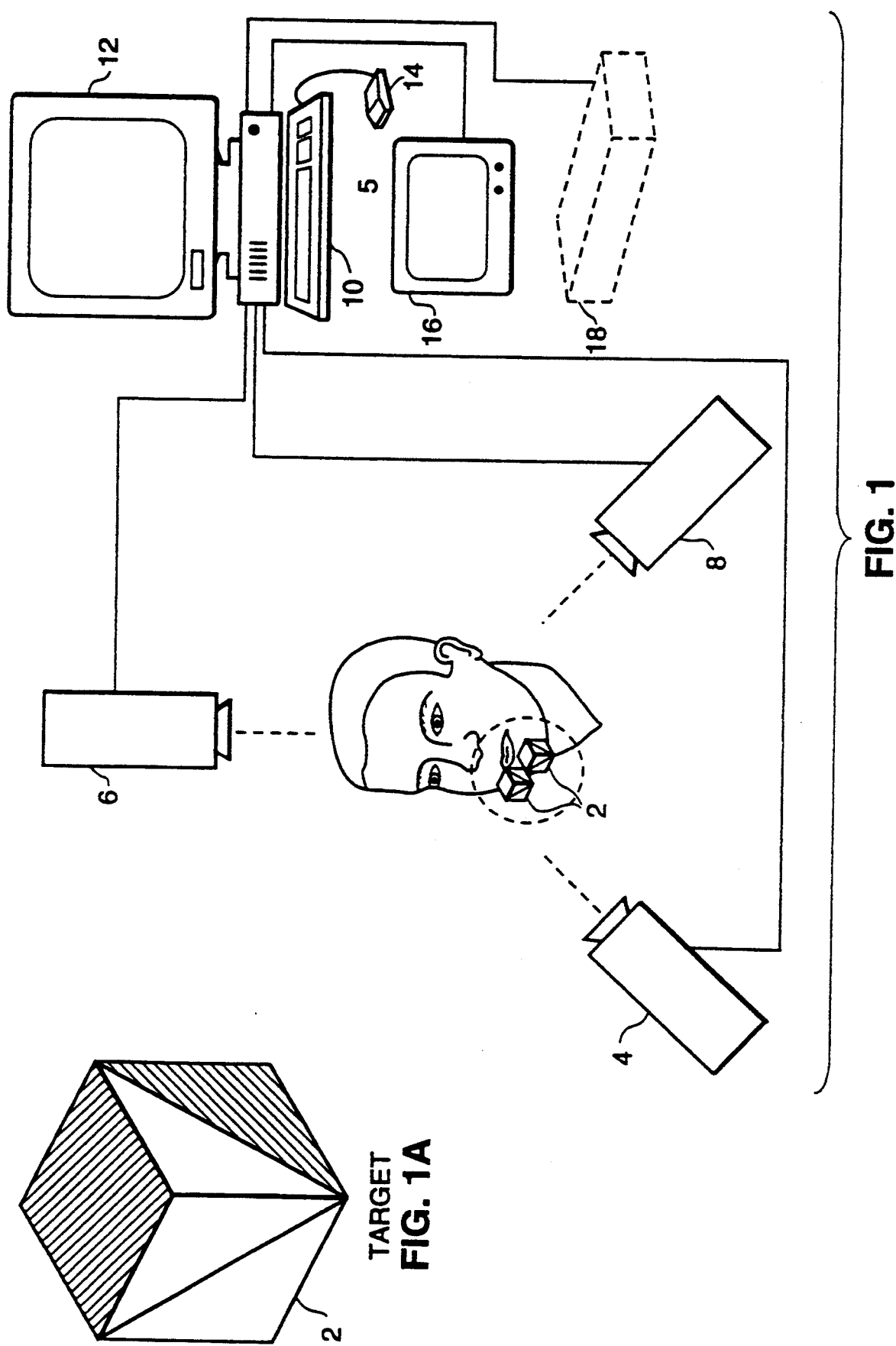
FIG. 1 shows the general arrangement of components and a typical target for the present invention.

FIG. 1 shows the arrangement of various components of a preferred embodiment of the present invention. The components include targets 2, cameras 4, 6 and 8, computer 10 having a pre-processor board, display 12, and mouse 14.

The cameras 4, 6, and 8 are arranged along orthogonal lines emanating from the center of the target zone. The camera optics are chosen to have a small field of view at a convenient distance, say 4 feet, from the target. The illumination and aperture is chosen to have a sufficient depth of field to maintain the targets in focus within the envelope of their travel.

The cameras can be either color or monochrome. There are differences in the pre-processor board for the two methods and the color cameras are described here. The color cameras provide the advantage that data from the upper and lower targets is isolated by color. This isolation of upper and lower targets simplifies the data processing.

The cameras communicate with the pre-processor board in the computer 10. The pre-processor provides the timing signals for the cameras and receives the video data. The data propagates from the pre-processor through the computer 10 for storage, display and additional processing.

The computer is a standard 386 or 486 Intel microprocessor type machine with either the industry standard bus, STD or EISA, or the IBM PS/2 bus. It has a high performance math co-processor. The computer includes a mouse 14 for use in tracing images, and for operating the graphical software interface. Mass storage is provided by hard disk and archiving by floppy and optical disk. Printing capability may also be provided.

The display 12 is a high performance color graphics device incorporating a separate intelligent driver board. The display hardware also operates in a conventional VGA mode for compatibility with standard software.

A small TV 16 is included for use in adjusting the chair and measurement cameras 4, 6, and 8. The TV is driven from a composite signal generated from the digital video data in the pre-processor board. In another embodiment, the display TV function could be provided by the computer graphics display.

The targets 2 have cross-hairs with high optical contrast on the visible surface of the targets. The pre-processor board will isolate the location of the target cross-hairs for each frame of data. Different colors are used for each face on the targets 2 so that the axes and targets can be isolated by color. The camera for each axis has a matching filter so that all light except that from the desired target face is attenuated. An optional embodiment would have internally illuminated targets.

Figure 9A:
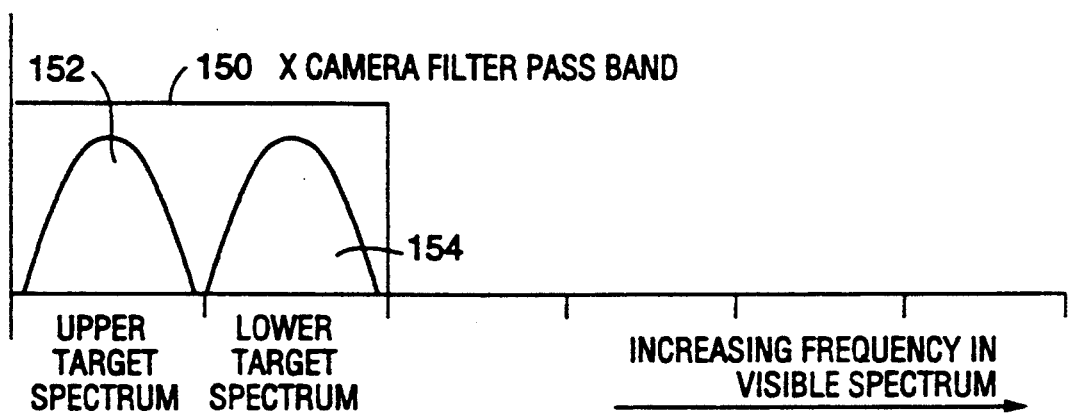
FIG. 9 shows spectral graphs illustrating how camera filters are used to separate target data.
Figure 9B:
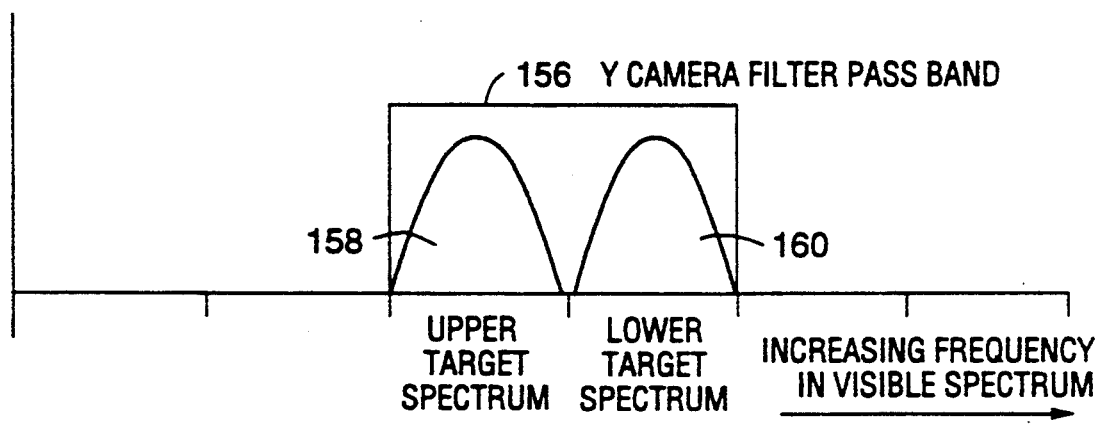
Figure 9C:
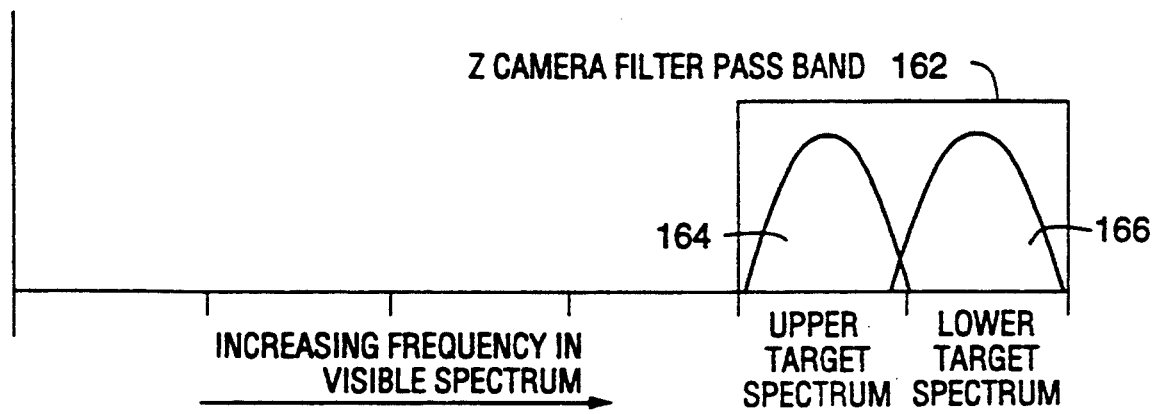

The visible spectrum is divided into 6 bands of wavelengths, each band corresponding to a color on one of the target faces. Each camera is equipped with a filter that passes light in two different adjacent bands. For each camera, and axis, one band will be for the upper target and the other for the lower target. The color separation provides the image isolation in the camera for the upper and lower targets. The wavelength bands are chosen so that the elements. This serves to simplify detection in the pre-processor board. The camera filter configurations are illustrated in FIG. 9, discussed below.

The targets 2 are preferably light in weight and capable of temporary attachment to the teeth with adhesive. Disposable targets simplify sanitization and are intended to be within scope of invention. A detachable and disposable target support arm may be used to extend the targets away from the subject's face, and this embodiment is intended to be within the scope of the present invention.

The computer 10 may also be connected to a motor adjusted articulator 18. The articulator 18 has stepper motors which are activated by a driver board inside the computer. The articulator 18 is automatically adjusted to correspond to the target positional data collected by the cameras.

Figure 2:
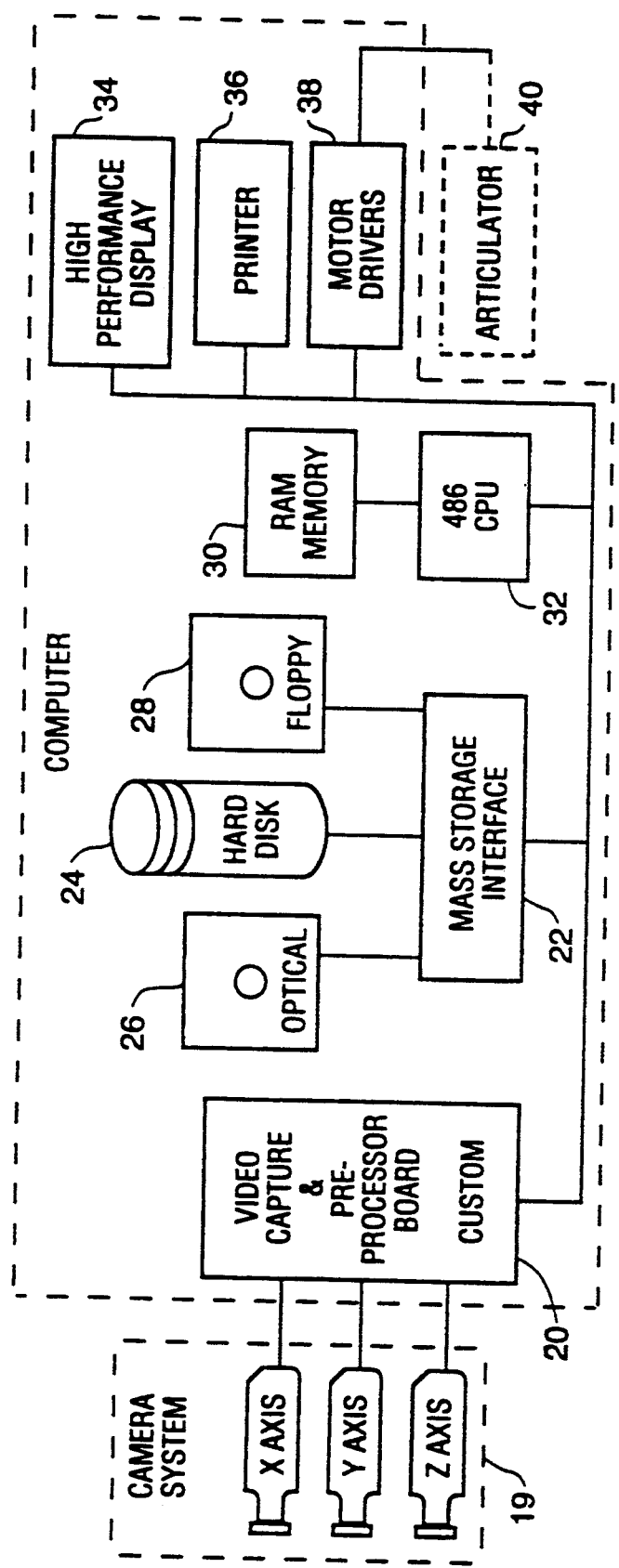
FIG. 2 is a block diagram showing the relationship between the components of the present invention.

In FIG. 2 a block diagram of the entire system is shown. The camera system 19 communicates with the pre-processor board 20. The cameras are matched to the pre-processor board. The timing and control signals for the camera system 19 are generated on the board 20. The cameras are Charge Control Device (CCD) type devices in which a single video chip receives the light image and converts it to an array of amplitude signals. The amplitude signals are read out one at a time by digital addressing circuitry. The pre-processor board 20 provides the timing signals for the cameras 19 and synchronizes them so that the data from all 3 axes are coordinated in time.

The pre-processor board 20 processes the video data, determining pixel by pixel if it represents a point on the target line. The addresses of those pixels on the target line are then saved to mass storage through the mass storage interface 22, for additional processing and display.

The computer can utilize numerous commercially available mass storage devices. With current technology, the hard disk 24 would be preferred for operating storage and the optical disk 26 for archiving. A floppy disc 28 can also be used for transporting the data, particularly if a different computer is used for adjusting the motor-driven articulator.

The RAM memory 30 and CPU 32 is used to process the positional data and to produce signals for the high performance display 34, printer 36, or motor drivers 38 for adjusting the articulator 40.

The display device 34 is compatible with the computer architecture and operating system but also is capable of display list processing. The actual display screen has at least 1000 by 768 pixels of resolution.

Printing devices 36 can be accommodated. These can be graphic and character printers of currently existing technology.

The motor drivers 38 for the articulator adjustment motors is a commercially available plug in board. An external power supply is required for the articulator motors 40.

Figure 3B:
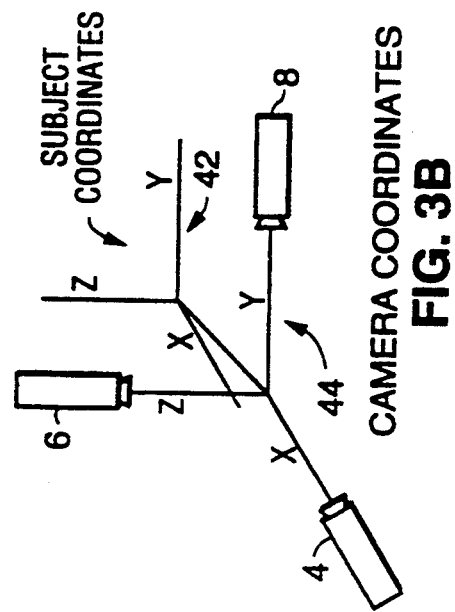
FIG. 3 shows the coordinate system around which measurements are made in the present invention.
Figure 3A:
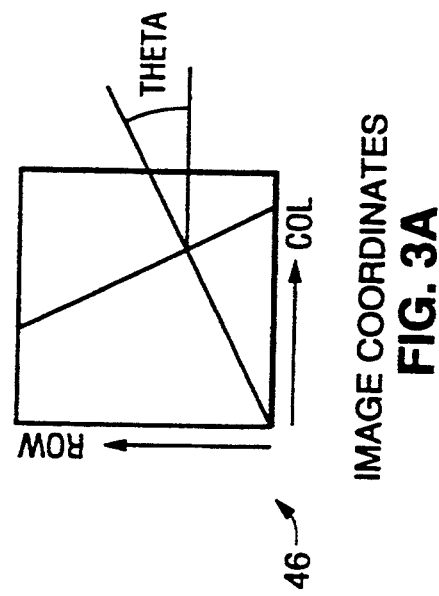

FIG. 3 shows the coordinate system about which measurements are taken in the present invention. Three physical coordinate systems are important to the understanding of the system. Additional virtual and screen coordinates are used in the software and display system but they are incidental to the operation. The displayed images will be a representation of the image in the Subject Coordinate system 42.

The three coordinate systems are, Camera Coordinates 44, Subject Coordinates 42 and Image Coordinates 46, as shown in FIG. 3. The Camera Coordinate system 44 defines the relative relationship between the three cameras. Its axes are X, Y and Z with corresponding angles. It is important that the computer know how the cameras are pointing and their relative spacing. A calibration procedure generates and captures that information. The subsequent coordinate transformations performed by the software requires knowledge of the actual physical arrangement. Optimum performance is achieved when the cameras are aimed at a common point at position (0,0,0) in the Camera Coordinate system.

The Subject Coordinate system 42 is where the measurements are being made. The positional reference is the subject's upper jaw. This has some displacement and rotation in the Camera Coordinates 44, which will be changing while capturing data. The cameras 4, 6, and 8 track the upper target so that the motion with respect to the Subject Coordinates system 42 is constantly updated in the computer. The displayed data is all relative to the Subject Coordinates 42. Coordinate transformations are programmed into the software that take data from the Image Coordinates 46 and reconstruct the image in the Subject Coordinates 42.

The Image Coordinate system 46 is found inside the camera on the CCD chip. The chip sees rows and columns of pixels which are addressed sequentially from 0,0 along each column and advancing at the end of each column to the next row. The target image the array of CCD elements (pixels) is the vital link between the subject and the computer. The absolute relationship between the cameras and the subject is not actually known, however the relative motion during the measurement interval is known. The absolute relationship is important only to the extent that certain linear approximations hold true.

Figure 4:
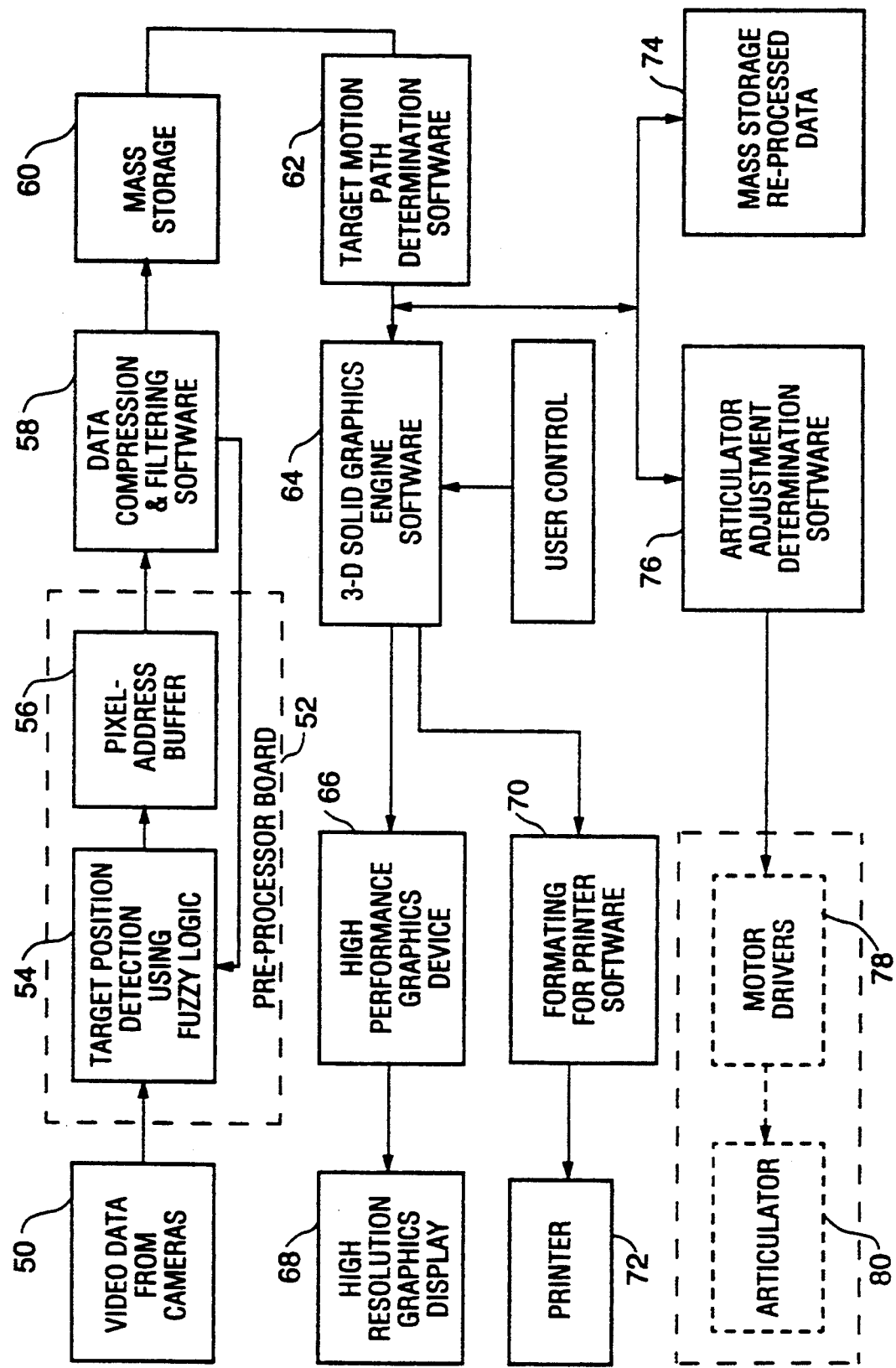
FIG. 4 is a block diagram showing data flow and processing in the present invention.

FIG. 4 is a block diagram showing how the data flows and is processed in the positional data collection and transformation steps of the present invention. Data flows from the video cameras 50 through the computer and hard disk mass storage 60 to the video display 68 and printer 72. The data is processed three times on its journey. The first data processing step occurs on the Pre-Processor board 52. The second data processing step is performed as the data is transferred from the Pre-Processing board to mass storage 60. The third data processing step occurs as the data is read from mass storage 60 and prepared for the display 68. The data is restored to hard disk after this third processing step.

Data from the video cameras 50 enters the pre-processing board 52 in synchronism with clock and timing signals generated by the pre-processing board 52. The data from each of the cameras enters the target position detectors 54 where it is transformed into a record of addresses of those pixels in the camera video chip which were exposed to light from a cross-hair on the target. The addresses are buffered 56 and transferred from the pre-processing board 52 to system RAM with DMA transfers. Advanced techniques are used to process the data on the pre-processing board. Artificial Intelligence Fuzzy Logic techniques are used to select legitimate target cross-hair addresses and minimize signal-related noise. In this way, accuracy is improved over that obtained by conventional threshold detection techniques because the "most likely" decision is made based on information about each pixel's neighboring pixels. The legitimate address detection criteria are continuously updated to maintain consistent output data. A more detailed discussion of the pre-processing board follows below.

A separate record is generated for each frame of video data obtained by each camera. For each video frame three records of data are created. For 1000×1000 pixel chips, each record would contain 4000 entries each of 20 bits (32 bit word). Each video frame creates 12000 words of address data. At 10 frames per second, 120,000 words of data is created per second. In a 30 second measurement, a total of 3.6 million words of data is generated.

The data is further qualified and processed as it is written to mass storage 60. Each record contains data from the two targets. This qualification and processing step separates the data from the two targets and puts it into separate records. If the software 58 detects inconsistent or unusable data, that information is fed back to the pre-processor board 52 for automatic adjustment of the detection criteria. The software 58 compresses the data by throwing out unnecessary or unusable records. It also locates and identifies those addresses near where the target cross hairs cross. This locus of points represents the true target position in the camera field of view. This point can be transformed back into the Subject's Coordinate system 42 in FIG. 3.

Positional data is retrieved from hard disk for display and other uses. The data is processed by software to reconstruct the target path 62. The retrieved data is scanned one frame at a time by algorithms that reconstruct the most likely location in Image Coordinates 46 of the target cross hairs in each frame. Each frame is by this method replaced by a new frame of temporary data. Each temporary frame consists of two records, one for each target, that contain the cross point address (row and column) and angle of rotation in the Image Coordinate system 46. The cross point is where the target cross hairs cross. This data which is in the Image Coordinate system 46 is then transformed into the Subject Coordinate system 42 frame by frame. The data in this final form is called re-processed data. This re-processed data is then saved to hard disk for quick retrieval 74.

The 3D graphics engine 64 manipulates the data and prepares it for display. The user has control 65 of the orientation and form of the displayed data. All of the display options such as solid, 2D plane, rotation, translation are provided by the graphics engine 64. The animated display is generated at this point. The software graphics engine 64 incorporates standard 3D graphics manipulation techniques. The capability to show an animated display is included. This is done by retrieving and displaying multiple frames of data in consecutive order.

From the graphics engine 64 the data propagates through the high performance graphics device 66 and ultimately to the display 51. The graphics hardware and display can be selected from standard high performance commercially available products such as Verticom Hx series, VTHX 16F2, Vermont Micro Systems, VMI-MIB3, Number Nine Computer, Pepper SGT Plus NNSGT+2, Control System Artist 12, CS12/16 and Renaissance GRX Rendition REII/256VGA.

An animated image of the teeth and jaw in relative motion is obtained by capturing special images of the patient's mouth with the frontal camera. Views of both the upper and lower teeth are taken. These views are then displayed on the screen and the operator then manually electronically traces the teeth or matches a standard form typically with the mouse 14. The displayed teeth image is corrected for the camera viewing angle by the graphics engine so that a view of correct perspective is presented. Calibration values must have been previously entered. The tracing is done using the mouse 14. Once the teeth are traced, the motion data is employed to limit the relative motion of the upper and lower jaws in the animation.

The re-processed data is also made available to the articulator adjustment software 76 where settings for the articulator 80 are determined. The limits of the measured motion serve to provide the information necessary to calculate the articulator settings. From this point the setting information is directed to the motor drivers 78 which cause the motors to adjust the articulator 80.

Figure 5:
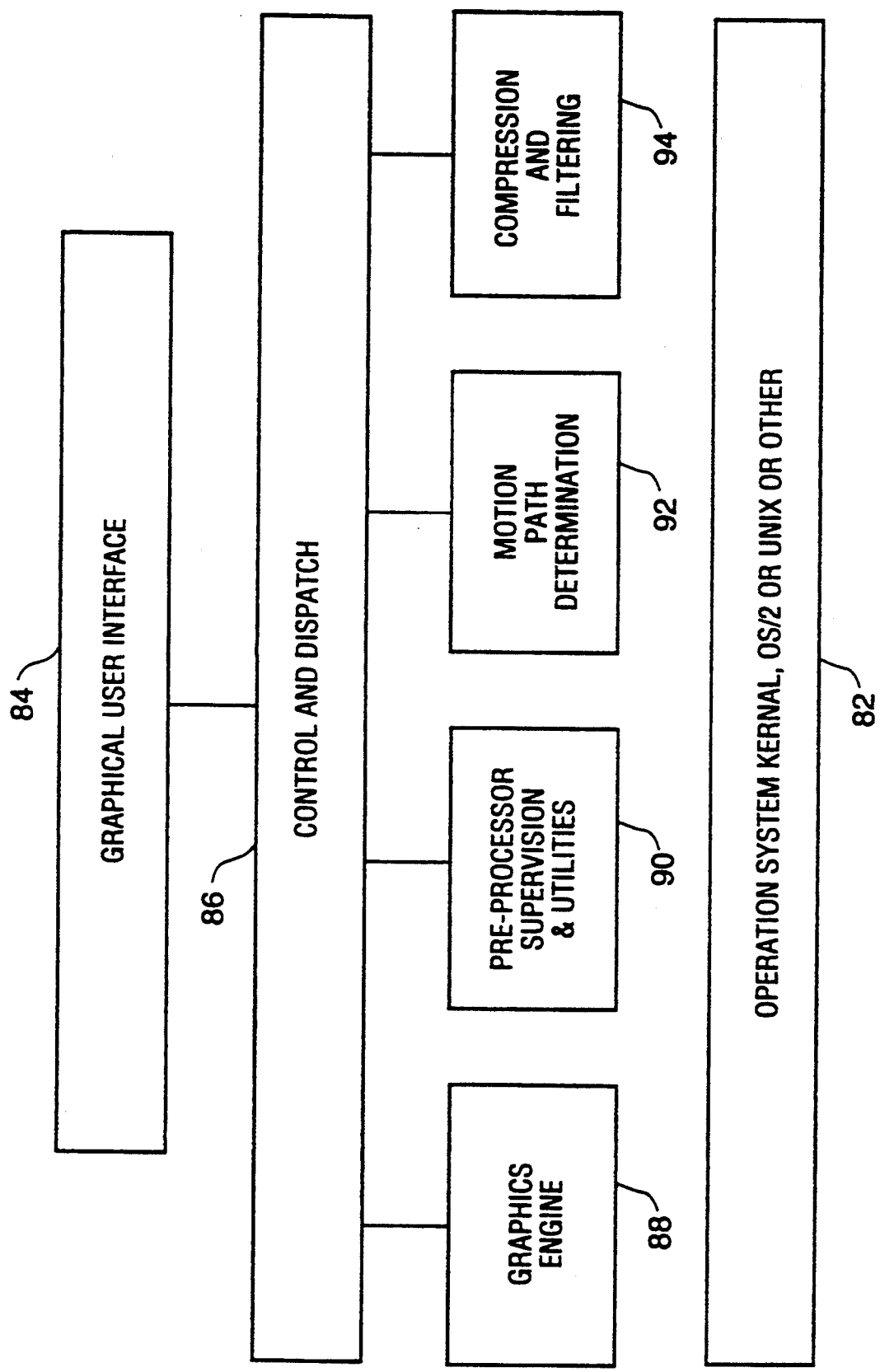
FIG. 5 is a block diagram showing the software organization in the present invention.

FIG. 5 shows the software organization. The software is designed around structured techniques and targeted for the OS/2 (or UNIX) operating systems 82. The software is written for the OS/2 environment but can be easily switched to a DNIX like operating system. OS/2 and UNIX provide a real time multi-tasking environment where communication, networking, printing and graphics are standardized. The software conforms to the standard graphical interface 70 of OS/2 however a special interface is provided for the high performance graphics device.

The user interface 84 is graphical with command driven mode available. The graphical user interface 84 conforms to the standards of the operating system 82. Underneath the user interface is the control and dispatch level 86. This level interfaces to the user controls and also the specific task modules. The actual control and supervision is provided at this level.

Task specific application modules reside under the control level 86. A Graphics Engine 88 performs all of the graphics generation, animation, display formatting and printer formatting functions. This graphics engine module interfaces to the operating system graphics utilities, to the high performances display card and to the printer driver module. Input control is derived from the control and dispatch level 86. All user input is directed through the dispatch level 86.

A Pre-Processor Supervision and Utilities module 90 performs all the direct control of the custom pre-processor board. It provides initialization and high level commands for the board. In addition this module handles the calibration of the system. A special calibration mode is provided where data on the camera arrangement is entered. The user entry of measured parameters from the patient is handled here as well. The utility functions such as motor-driven articulator adjustment are provided in this module.

Another task specific module is for Motion Path Determination 92. The data processing occurs in three steps. The first step takes place on the pre-processor board 52 where the video data is converted to records of addresses corresponding to target lines on the video chip. The second step occurs during the transfer of data from the pre-processor board 54 to mass storage 60. In this second step, the data from the two targets (upper and lower jaw targets) are separated, and unqualified data discarded. The location of the target center is identified. The third step is performed by the Motion Path Determination module 92. This third step takes the target data in the Image Coordinate system 46 and transforms it into the Subject Coordinate system 42. In this form, the data is ready for the graphics engine 88 and it is referred to as re-processed. This re-processed data is saved to hard disk for fast retrieval.

The Compression and Filtering module 94 performs the second stage of data processing. The data is read from the Pre-Processor into system RAM with a DMA cycle. This module picks the data up from RAM, performs some additional processing, and saves it to hard disk mass storage. The data is separated into two groups of records, one for each target. The records from each camera are included. In addition, the data are examined with incomplete or inconsistent data being discarded. If the data becomes unreliable, the module will signal the pre-processor board to alter the detection criteria.

Figure 6:
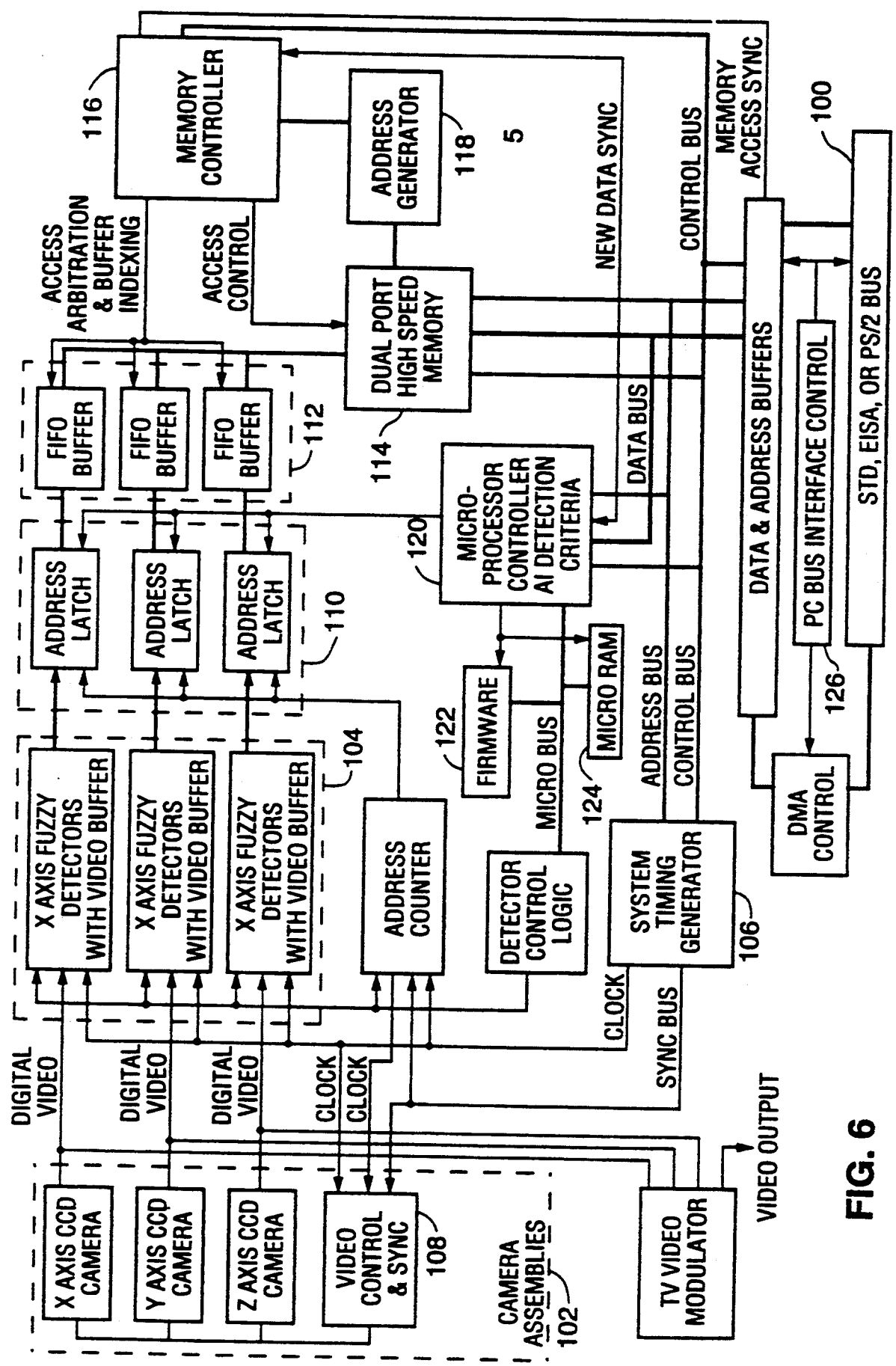
FIG. 6 is a block diagram showing the organization of the pre-processor board of the present invention.
Figure 7B:
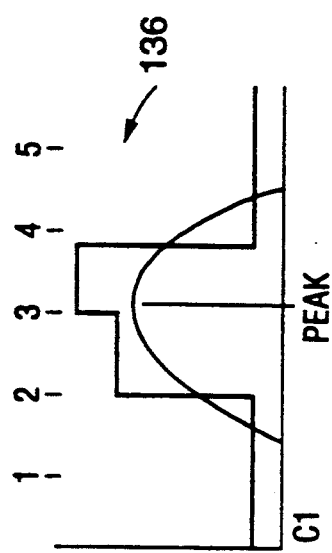
FIG. 7 is an example illustrating how data is detected in the present invention.
Figure 7C:
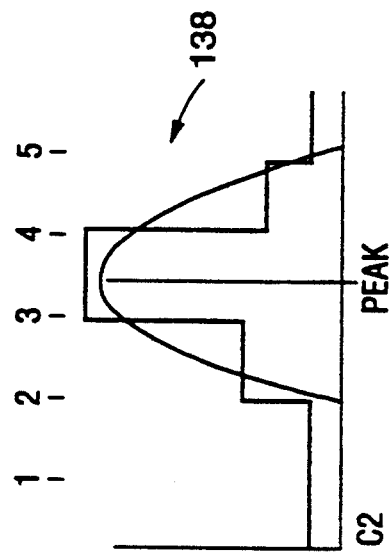
Figure 7D:
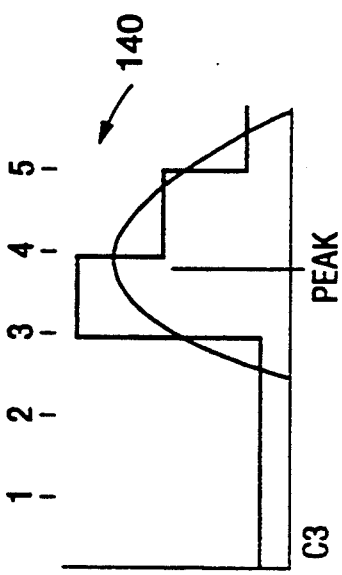
Figure 7A:
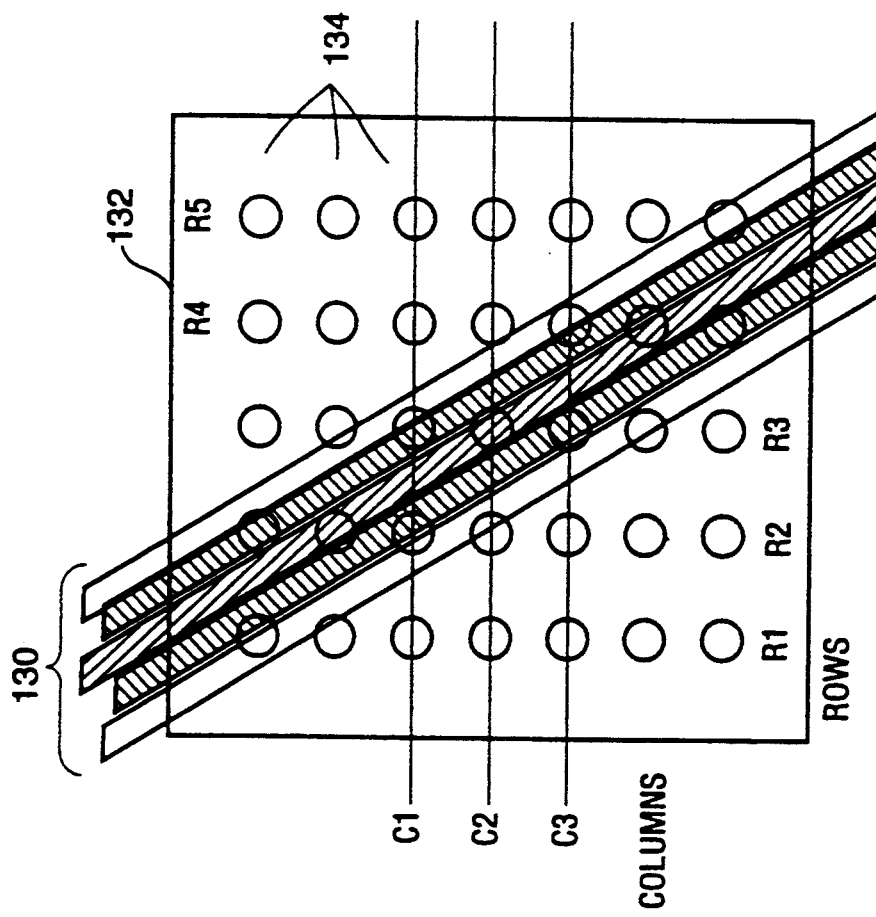

FIG. 6 shows the design of the Pre-Processor Board. The Pre-Processor is a custom electronic plug-in board for the IBM type desk top computer. It is designed for the STD(IBM AT) bus, the EISA bus and the IBM PS/2 bus 18 100.

The Pre-Processor Board receives the data from the video cameras 102 and simplifies it to records of address data. The addresses are of those pixels which are influenced by the image of the target cross hairs on the camera COD array. The addresses are fractional so that the resolution is to the nearest one-quarter ($\frac{1}{4}$) address step. Fuzzy Logic detectors 104 are employed to provide the most accurate determination of the target position. Raw data from the camera is received at ten frames per second. At a million pixels per frame from three cameras at total of three (3) million pixels per second of data is generated. Each pixel requires one word of memory. The Pre-Processor board reduces this three million words per second requirement to 120,000 words per second.

The System Timing Generator 106 provides timing signals for the cameras and it also synchronizes them so that the data from all 3 axes are coordinated in time. Bi-directional timing signals between the board and the cameras are carried by the Video Control and Sync Bus 108.

The video data takes the form of an analog voltage which is digitally clocked out of the pixel array one pixel at a time. A start signal from the timing generator 106 synchronizes address counters in each camera. A common clock signal is fed from the pre-processor board to the camera assembly 102 so that the addresses are synchronized. The address counters then increment one count with each clock pulse.

The video data from the addressed pixel is directed to respective fuzzy detector 104 where it is stored in a buffer. The fuzzy detectors hold several pixels of data in a buffer so that the values of the neighboring pixels values are available for the detection algorithm.

The detectors are further described below. The output from the detectors are addresses of pixels that were on the center line of the target image. The addresses have fractional resolution of one-quarter ($\frac{1}{4}$) address step. This precision results from the detection method.

The address data are latched 110 and then transferred into a FIFO buffer 112. From the buffer 112, the data are saved into a high speed dual port RAM 114 that is resident on the board. From the high speed memory, the data is then moved into the computer's memory with DMA transfers.

A memory controller 116 synchronizes the movement of the data from the FIFO buffers 112, through the high speed memory 114 and into the computer memory. The memory controller 116 generates buffer unload signals and write enable signals to the dual port RAM 114. The address generator 118 maintains the pointers to the data in the RAM. The high speed memory is organized as a circular buffer. The DMA transfers the data out to the computer as fast as it comes in. The high speed memory serves as a buffer between the system resource and the camera data stream.

A micro-processor 120 is embedded into the board logic. This processor provides supervisory control of the board, the cameras, and most importantly adjusts the coefficients of the detection algorithm. The performance of the detectors is monitored by the microprocessor 120 and corrections to the detector settings are fed back as required. Firmware 122 and micro ram 124 are associated with the micro-processor 120.

The microprocessor 120 has access to the data in the high speed memory 114. This data is periodically analyzed by the microprocessor 120 to determine the performance of the detectors 104. If the data indicates that the detectors are either missing blocks of data or including too much erroneous data, then the microprocessor 120 will command the changes to the logic and coefficients in the detectors 104.

The DMA transfer of data is initiated from the pre-processor board and completed by the computer.

The interface to the PC bus is managed by PC Bus Interface Control block 126.

FIG. 7 shows how the detector and the detection logic combine to enable the system to operate. A single color system is described. However, three color capability is provided in the camera and pre-processor board. The other two colors are similarly detected and processed. FIG. 6 shows an example of light from the target cross hair 130 falling on a portion of the video CCD chip 132. An array of pixels 134 on the CCD chip 132 is shown. Those pixels which are near the cross-hair image are illuminated. Data from the pixels is analog. The data is clocked out from the camera one pixel at a time. The analog data line has a voltage value corresponding to the quantity of light at the sensitive frequency (color) that impinges upon the addressed pixel at that moment.

The data is scanned out of the camera column by column and one pixel at a time. As the chosen pixels cross the illuminated area of the chip, the analog video data first increases and then decreases. As shown in the FIG. 7, the exact grouping of pixels and the amount of light each receives depends upon the angle of the camera to the target and physical layout of the chip. In the example shown, the image is about 3 pixels wide. The light intensity is peaked at the center of the band and decreases in intensity as the distance from the center increases.

The graphs 136, 138 and 140 show the light intensity as the point of observation moves across the chip for the three columns C1, C2 and C3. FIG. 7 shows the instantaneous analog value received from the addressed pixel with the light intensity distribution superimposed. This example shows the variability that is experienced in practice. The detector is able to reliably determine the location of the peak of the target light distribution.

Typically, the peak of the light distribution falls between pixels. To provide maximum resolution, the detector locates the peak within one-quarter (¼) of an address interval in space. This is to within one-quarter (¼) of the distance between pixels. The address number is increased in length by two bits to provide this additional resolution.

Figure 8A:
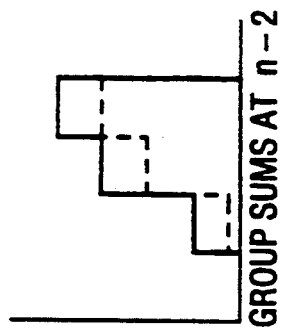
FIG. 8 is a detector block diagram.
Figure 8B:
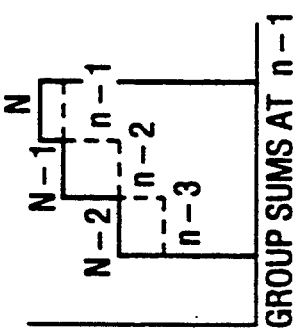
Figure 8C:
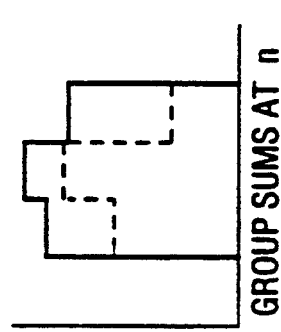
Figure 8:
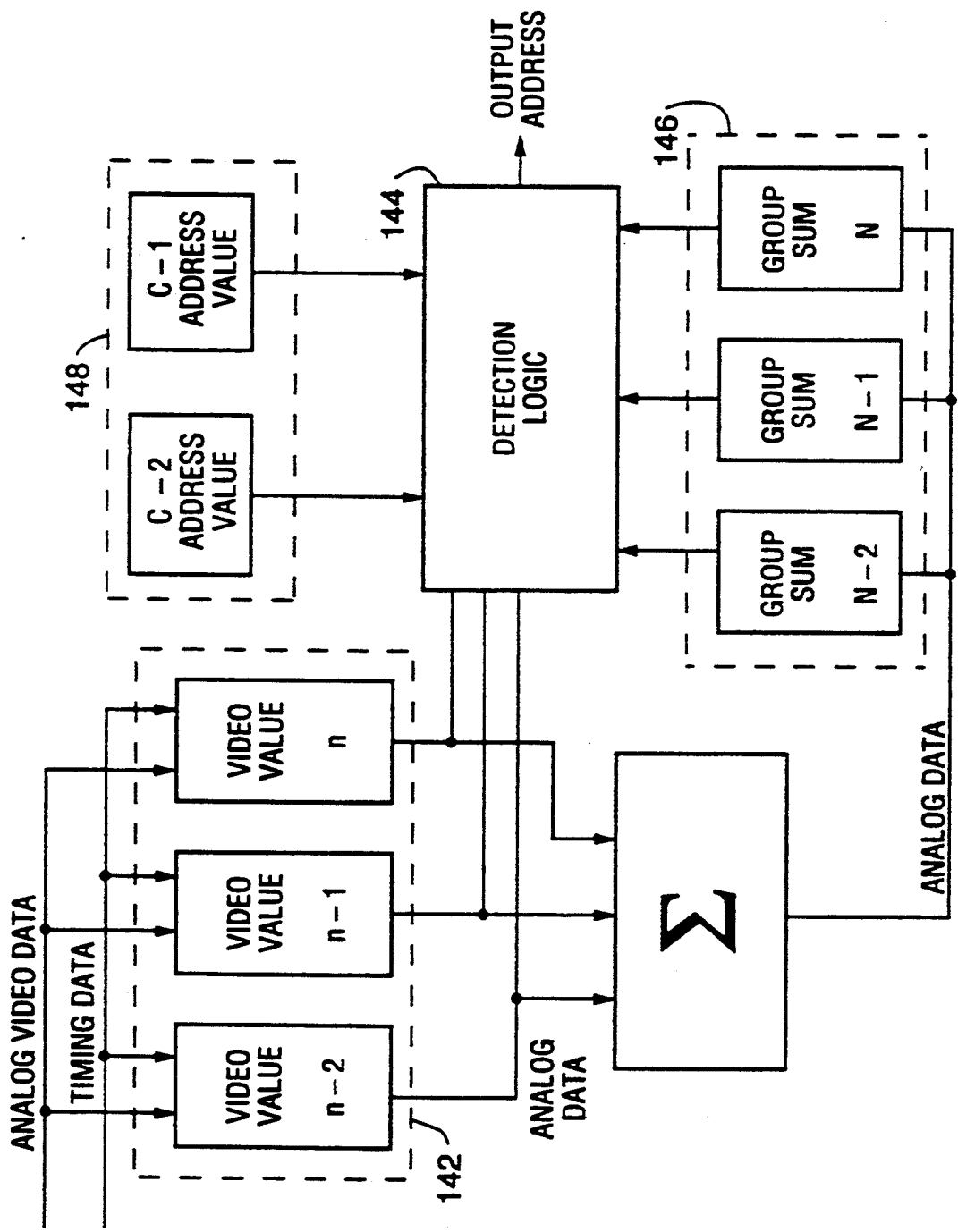

FIG. 8 is a Detector Block Diagram. The data plotted in FIG. 7 is from three consecutive columns. The process for collecting the data from one column is shown in FIG. 8. The Video Value blocks n, n-1 and n-2 142 are storage elements for the analog video data taken at address time n, n-1 and n-2. The number of storage elements can be increased if necessary to accommodate a larger target image.

The data is clocked into these Video value storage blocks from the camera. The most recent data is in block n. Pointers to these blocks are changed each time new data is loaded. The data is not actually moved between blocks. The analog blocks are sample and hold type operational amplifiers. Optionally, the signal could be digitized first and saved in digital form. Referring to FIG. 7, the data for C3 Rows R2, R3 and R4 could be in blocks n, n-1 and n-2 respectively.

The analog data is made available directly to the detection logic 144 where iris compared for amplitude. In addition, the data is summed and saved in additional blocks, "Group Sum" N,N-1 and N-2 146. As the data from a column is processed, the peak value along that column is located. This peak represents very closely the center of the illuminated area. The Group sum blocks 146 facilitate location of the maximum value. A further qualification of the data is done by reference to the detected image center on the previous columns, C-1 and C-2 148. It is expected that the data from a column will have consistent correlation with that from previous columns. If the data is inconsistent, then either the end of a target cross hair is involved or noise is present.

The output from the detection logic 144 is an address to the nearest of the center of the target cross hair in a column (frame) of data. The address is carried to 4 times greater resolution than that provided by the pixel spacing. When two targets appear simultaneously on the video chip, then the detectors will find two sets of addresses. The data from the two targets is separated spatially. Data from the video cameras enters the preprocessing board in synchronism with clock and timing signals generated by it.

FIG. 9 illustrates how each camera can be equipped with a different filter, so that data from differently colored target sides can be easily separated. Each camera lens is focused along its respective camera coordinate on an upper target side and a lower target side.

The X camera filter pass band 150 includes upper target spectrum 152 and lower target spectrum 154. The Y camera filter pass band 156 includes upper target spectrum 158 and lower target spectrum 160. The Z camera filter pass band 162 includes upper target spectrum 164 and lower target spectrum 166. The filters operate to exclude most light other than that received from the target faces, while simplifying pre-processor board data detection.

While the present invention has been described with reference to a particular embodiment, which utilizes specific hardware and software configurations, it will be readily apparent to those of ordinary skill in the art that modifications can be made to the described embodiment which are still within the scope of the present invention.

What is claimed is:

1. An apparatus for tracking and recording a subject's jaw motion, comprising:
   at least two targets, each target having at least one cross-hair disposed on a face of the target;
   means for non-intrusively attaching a first target to said subject in a fixed relationship relative to the subject's upper jaw, and means for non-intrusively attaching a second target to said subject in a fixed relationship relative to said subject's lower jaw, said targets being initially located near the origin (0,0,0) of a three dimensional subject coordinate system which coordinate system is fixed relative to said subject's upper jaw;
   three video cameras disposed about said subject's head, and disposed along camera coordinates X,Y and Z, each of said video cameras being positioned so that its lens is focused on said targets' cross-hairs, each of said cameras having a charge control device chip which includes an array of light sensitive pixels defining a two dimensional image coordinate system for converting a light image indicative of a target's cross-hair position into a series of amplitude signals;
   wherein each of said targets is approximately cuboidal with at least three differently colored faces oriented toward said cameras along camera coordinates X, Y and Z, each of said colored faces having a cross-hair of high optical contrast relative to its background; and
   computer means for receiving and processing said camera chip amplitude signals, said computer means having a pre-processor board for timing, synchronizing and transforming said camera chip amplitude signals into an address record representing said targets' relative positions as a function of time, said computer means further including a mass storage unit for storing the address record information.

2. The apparatus of claim 1, wherein each of said cameras is provided with color filter means for enhancing the target images.

3. The apparatus of claim 2, wherein said filter means includes a filter adapted to pass first and second adjacent wavelength bands, said first wavelength band corresponding to the first target's facial color along the respective camera coordinate, and the second wavelength band corresponding to the second target's facial color along the same respective camera coordinate, whereby wavelengths outside said wavelength bands are substantially blocked from the camera's charge control device chip.

4. An apparatus for tracking, recording and analyzing a subject's jaw motion comprising:

at least two targets, each target having at least one cross-hair disposed on a face of the target;

means for non-intrusively attaching a first target to said subject in a fixed relationship relative to the subject's upper jaw, and means for non-intrusively attaching a second target to said subject in a fixed relationship relative to said subject's lower jaw, said targets being initially located near the origin (0,0,0) of a three dimensional subject coordinate system which coordinate system is fixed relative to said subject's upper jaw;

three video cameras disposed about said subject's head, and disposed along camera coordinates X,Y and Z, each of said video cameras being positioned so that its lens is focused on said targets' cross-hairs, each of said cameras having a charge control device chip which includes an array of light sensitive pixels defining a two dimensional image coordinate system for converting a light image indicative of a target's cross-hair position into a series of amplitude signals;

wherein each of said targets is approximately cuboidal with at least three differently colored faces oriented toward said cameras along camera coordinates X, Y and Z, each of said colored faces having a cross-hair of high optical contrast relative to its background; and computer means for receiving and processing said camera chip amplitude signals, said computer means having a pre-processor board for timing, synchronizing and transforming said camera chip amplitude signals into an address record representing said targets' relative positions as a function of time, said computer means further including a mass storage unit for storing the address record information, graphics software for creating a simulation of said subject's jaw movement in said subject coordinate system based on said address record information, and display means for visually presenting said graphics means for visually presenting said graphics software simulation of jaw movement.

5. The apparatus of claim 4, wherein each of said cameras is provided with color filter means for enhancing the target images.

6. A method for tracking, recording and analyzing a subject's jaw motion, comprising the steps of:

non-intrusively attaching at least two targets having cross-hairs disposed on the target face to the subject, such that a first target is in a fixed relationship relative to said subject's upper jaw, and a second target is in a fixed relationship relative to said subject's lower jaw, said targets being initially located near the origin (0,0,0) of a three dimensional subject coordinate system which is fixed relative to said subject's upper jaw;

operating three video cameras disposed about said subject's head and disposed along camera coordinates X, Y and Z, each of said video cameras being positioned so that its lens is focused on said targets' cross-hairs, and each of said cameras having a charge control device chip which includes an array of light sensitive pixels defining a two dimensional image coordinate system for converting a light image indicative of a target's cross-hair position into a series of amplitude signals; and receiving and processing said camera chip amplitude signals in computer means, said computer means including a pre-processor board for timing, synchronizing and transforming said camera chip amplitude signals into an address record representing the targets' relative positions as a function of time, said computer means further including a mass storage unit for storing said address record information, graphics software for creating a simulation of said subject's jaw movement in said subject coordinate system based on said address record information display means for visually presenting said graphics software simulation of jaw movement, and printer means.

7. The method of claim 6, further comprising the step of:

printing a dental pantograph depicting said subject's jaw movement as simulated by said computer means graphic software.

* * * * *

UNITED STATES PATENT AND TRADEMARK OFFICE
CERTIFICATE OF CORRECTION

PATENT NO. : 5,340,309
DATED : August 23, 1994
INVENTOR(S) : James G. Robertson

It is certified that error appears in the above-indentified patent and that said Letters Patent is hereby corrected as shown below:

In Col. 13, lines 43 and 44, delete "means for visually presenting said graphics".

In Col. 14, line 36, after "tion", insert --,--.

Signed and Sealed this

First Day of November, 1994

*Attest:*

BRUCE LEHMAN

*Attesting Officer*     *Commissioner of Patents and Trademarks*